United States Patent
Liu et al.

(10) Patent No.: US 7,459,173 B2
(45) Date of Patent: Dec. 2, 2008

(54) MEDICAMENT FOR PREVENTION AND TREATMENT OF BONE FRACTURE AND OSTEOPOROSIS

(75) Inventors: Suying Liu, Linkou Township, Taipei County (TW); Yiming Tsal, Linkou Township, Taipei County (TW)

(73) Assignee: Sagittarius Life Science Corp., Taipei County (TW)

( * ) Notice: Subject to any disclaimer, the term of this patent is extended or adjusted under 35 U.S.C. 154(b) by 626 days.

(21) Appl. No.: 10/976,599

(22) Filed: Oct. 28, 2004

(65) Prior Publication Data

US 2006/0093619 A1  May 4, 2006

Related U.S. Application Data

(63) Continuation of application No. PCT/CN02/00534, filed on Aug. 2, 2002.

(51) Int. Cl.
*A61K 36/28* (2006.01)
*A61K 36/83* (2006.01)
*A61K 36/899* (2006.01)
*A61K 36/324* (2006.01)
*A61K 36/284* (2006.01)
*A61K 36/39* (2006.01)
*A61P 19/10* (2006.01)

(52) U.S. Cl. ............... 424/750; 424/725; 424/773; 424/776; 424/775; 424/777; 424/451; 424/464

(58) Field of Classification Search .............. None
See application file for complete search history.

(56) References Cited

U.S. PATENT DOCUMENTS 6,333,312 B1 * 12/2001 Kuberasampath et al.

FOREIGN PATENT DOCUMENTS

| CN | A 1079160 | 8/1993 |
|---|---|---|
| CN | A 1134286 | 10/1996 |
| CN | A 1318391 | 10/2000 |
| CN | A 1277848 | 12/2000 |
| CN | 1457822 | * 11/2003 |

* cited by examiner

*Primary Examiner*—Michele Flood
(74) *Attorney, Agent, or Firm*—WPAT, P.C.; Anthony King (57) ABSTRACT

A pharmaceutical composition which can be used to prevent and treat bone fracture and osteoporosis. The composition is composed of *Semen lactucae sativae* 0.1-1, *Lignum aquilariae resinatum* 2-20, *Fructus oryzae* 1-5, *Resina boswelliae carterii* 0.1-1, *Rhizoma atractylodis macrocephalae* 0.1-1 and *Semen cuscutae* 0.1-1. The whole or the specific parts of the plants can be used to prepare the inventive pharmaceutical composition; preferred plants are *Aquilariae lignum* containing resin and *Boswellia carterii* containing resin. This pharmaceutical composition can be formulated into lozenge, tablet, film coated tablets, capsule, soft capsule, granule, powder, pill, solution, emulsion, injection solution, injection, ointment, cream, spray or inhalant.

6 Claims, 9 Drawing Sheets

MEDICAMENT FOR PREVENTION AND TREATMENT OF BONE FRACTURE AND OSTEOPOROSIS

CROSS-REFERENCE TO RELATED APPLICATIONS

This application is a continuation of International Application No. PCT/CN02/00534, filed Aug. 02, 2002.

FIELD OF INVENTION

The present invention concerns a medicine to prevent and to treat bone fracture and osteoporosis. In particular, it relates to a preparation comprising Chinese herbs, its manufacture processes and its usages. The effectiveness and safety of the present invention on prevention and treatment of bone fracture and osteoporosis are proven by in vitro and in vivo studies in mammals.

BACKGROUND OF THE INVENTION

Osteoporosis is a devastating condition in all population at all ages. The prevalence rate increases with age. Generally, the porous bones become thin, brittle, and easily broken, especially at carpus, femur, and vertebrae. The most apparent syndromes of osteoporosis are vertebral compressive fractures that lead to back pain, shortening of height, and kyphosis. The bone mineral density (BMD) peaks at 35 to 40 years old in human. Women at age 50 during menopause lose bone mineral at the rate of 1 to 3% yearly and the bones become porous. The prevalence of osteoporosis in women is twice that of men.

The action mechanism of currently available therapeutics, for examples, bisphosphonates, specific estrogen receptor modulator, calcitonin, and estrogen, are mostly inhibiting the activity of osteoclasts. Parathyroid hormone is the only one that is working on stimulation of osteoblasts. There are many undesirable side effects and their long-term safety are not clear. Unfortunately, osteoporotic patients need to take these medications in a very long term. Among these medications, calcitonin and parathyroid hormones are peptide in nature. They need to be administered by daily injections or inhale that are not user-friendly to the patients.

The worldwide trend on natural modality of health care on osteoporosis is limited to high calcium diet of milk, dairy products, fishes, soy and deep green leaves, and weight-bearing exercises. The prior arts have taught some natural foods or herbs that had effects on prevention or treatment of osteoporosis. For examples, Diane Feskanich reported that women took one serving of lettuce per day had 45% less chance to get femur fracture than women took less than one serving per week. The authors suggested that vitamin K in lettuce was the active component (Am. J. Clin. Nutr. 69: 74-79, 1999). The present invention comprises seeds of lettuce, and the preparation does not contain vitamin K. L. Cui. Y. F. Ma reported that oral gavage of water extract of *Epimedium sagittatum maxim, Astragalus mimbranaecus,* and *Rhizoma attractylodis macrocephalae* at 1.0 g/Kg to ovariectomized rats was able to prevent mineral loss and increase bone mass (J. Bone and Mineral Res. 14 (Suppl 1): S283, 1999). The herbal composition of the present invention is different from the aforementioned disclosures, and the present invention shows better effect on the increase in BMD than the aforementioned disclosures.

Hu X. disclosed in China patent number CN1099294 in 1995, that powder containing *Gypsum Fibrosum, Cinnamomi Ramulus, Citri Tankan Exocarpium, Ephedrae Herba, Paeoniae Radix, Ponciri Trifoliatae Fructus, Rhizoma Chuanxiong, Poria, Moutan Cortex, Rhizoma Pinelliae, Rhizoma Atractylodis Macrocephalae, Magnoliae Cortex, Scutellariae Radix, Citri Reticulatae Pericarpium, Perillae Fructus, Codonopsis Pilosulae Radix, Angelicae Sinensis Radix, Bupleuri Radix, Aconiti Lateralis Preparata Radix, Semen Juglandis* showed activities of anti-inflammation in bone marrow and treated osteomyelitis and hyperosteogeny. However, the composition of this 20 herbs containing preparation was different from the composition of the present invention, and the claim of the aforementioned disclosure was for anti-inflammatory activity, not for preventing and treating bone fracture and osteoporosis as the present invention. Lui, H. disclosed in China patent number CN1079160 in 1993, that powder containing *Aquilariae Resinatum Lignum, Flos Carthami, Aucklandiae Radix, Rhizoma Chuanxiong, Cinnamomi Ramulus, Eupolyphaga Seu Steleophaga, Rhizoma Drynariae, Semen Strychni, Achyranthis Bidentatae Radix, Semen Cucumis, Herba Abri, Rhizoma Rhei, Pyritum, Borneolum* and *Sanguis Draconi* improved the function of kidney, and was able to treat the defects in bone and cartilage development. However, the composition of this 18 herbs containing preparation was different from the composition of the present invention, and this disclosure did not present any well controlled study to support its efficacy on curing bone fracture and osteoporosis. Masuko Shiyouji et. al. disclosed in Japan patent number JP4266820 in 1992, that carbon number 22 to 38 long chain saturated alcohol was able to prevent bone mineral loss and promote bone formation; however, in the aforementioned patent, the composition was extracted and purified from wheat germ oil or rice bran oil by alcohol, that was different from the present invention. The present invention comprises seeds of *Fructus Oryzae* without the bran, not of wheat germ oil or rice bran oil. Other prior arts, with compositions different from the present invention, such as China patent number CN1195697, CN1266696, CN1180530, CN1287853, CN1181958, CN1071843, CN1219428, CN1245711, CN1312096, CN1113440, CN1083727 and CN1277848, claimed for their usefulness in treating bone fracture based on Chinese medicinal theories without experimental data or well controlled studies to support the effectiveness of their claims. The present invention with composition different from all of the aforementioned patents and publications demonstrates its efficacies on preventing and treating bone fracture and osteoporosis by both in vitro and in vivo studies. The present invention provides a new composition from a herbal combination that is able to prevent and treat bone fracture and osteoporosis by a natural therapeutic modality.

SUMMARY OF THE INVENTION

On compensating the insufficiency of prior arts, one embodiment of the present invention is to provide a new herbal composition for the prevention and treatment of bone fracture and osteoporosis.

Another embodiment of the present invention is to provide a method of manufacture processes to prepare a new herbal composition for the prevention and treatment of bone fracture and osteoporosis.

Yet, another embodiment of the present invention is to provide an application of a new herbal composition for the prevention and treatment of bone fracture and osteoporosis, and a method of application of a new herbal composition for the prevention and treatment of bone fracture and osteoporosis.

The present invention provides an herbal composition comprises *Semen lactucae sativae, Lignum aquilariae resinatum, Fructus oryzae, Resina boswelliae carterii, Rhizoma atractylodis macrocephalae* and *Semen cuscutae* at the ratio of 0.1-1:2-20:1-5:0.1-1:0.1-1:0.1-1. The more preferable ratio is 0.5:5:2:0.5:0.25:0.5.

According to the present invention, *Lignum aquilariae resinatum* can be resin containing *Lignum aquilariae resinatum*, and *Resina boswelliae carterii* can be resin containing *Resina boswelliae carterii*. By employing with pharmaceutically acceptable excipients, carriers or diluents, the herbal combination of the present invention can be formulated into various dosage forms including, but not limiting to, lozenge, tablet, film coated tablet, capsule, soft capsule, granule, powder, pill, solution, emulsion, injection solution, injection, ointment, cream, spray or inhalant.

The present invention employs a method of preparing an herbal combination. The processes include the following steps:

(1). Extraction of *Semen lactucae sativae, Lignum aquilariae resinatum, Fructus oryzae, Resina boswelliae carteri, Rhizoma atractylodis macrocephalae* and *Semen cuscutae*.

(2). Mixing the effective amount of the extract with pharmaceutically acceptable carriers, excipients or diluents to make into the expecting dosage forms.

The herbal composition of the aforementioned methods comprises *Semen lactucae sativae, Lignum aquilariae resinatum, Fructus oryzae, Resina boswelliae carterii, Rhizoma atractylodis macrocephalae* and *Semen cuscutae* at the ratio of 0.1-1:2-20:1-5:0.1-1:0.1-1:0.1-1. The more preferable ratio is 0.5:5:2:0.5:0.25:0.5.

*Lignum aquilariae resinatum* can be resin containing *Lignum aquilariae resinatum*, and *Resina boswelliae carterii* can be resin containing *Resina boswelliae carterii*.

By employing the aforementioned method, with pharmaceutically acceptable excipients, carriers or diluents, the herbal combination of the present invention can be formulated into various dosage forms including, but not limiting to, lozenge, tablet, film coated tablet, capsule, soft capsule, granule, powder, pill, solution, emulsion, injection solution, injection, ointment, cream, spray or inhalant.

The present invention provides a method to prevent and to treat bone fracture and osteoporosis by administering an effective dose of the present herbal composition via oral, intramuscular, intravenous, mucosal or topical applications.

More specifically, the herbal composition of present invention is useful in preventing and treating bone fracture and osteoporosis. The herbal composition comprises various ratios of *Semen lactucae sativae, Lignum aquilariae resinatum, Fructus oryzae, Resina boswelliae carterii, Rhizoma atractylodis macrocephalae* and *Semen cuscutae*. In one preferred embodiment, the herbs can be the whole plants or specific parts of the plants. *Semen Lactucae Sativae* is the dry semen from *Lactuca sativa L.* of Composite family of plant. *Lignum Aquilariae Resinatum* is the resin-containing trunks from *Aquilaria agallocha Roxb.* or *Aquilaria sinensis Gilg.* of *Thymelaeaceae* family of plant, *Fructus Oryzae* is the fruit from *Oryza sativa L.* of Gramineae family of plant, *Resina Boswelliae Carterii* is the resin from *Boswellia carterii Birdw.* of Burseraceae family of plant, *Rhizoma Atractylodis Macrocephalae* is the dry rhizoma from *Atractylodes macrocephala Koidz.* of Composite family of plant, and *Semen Cuscutae* is the dry semen from *Cuscuta chinensis L., Cuscuta australis R. Br.,* or *Cuscuta japonica choisy* of Convolvulaceae family of plant.

The prevent invention comprises *Semen lactucae sativae, Lignum aquilariae resinatum, Fructus oryzae, Resina boswelliae carteri, Rhizoma atractylodis macrocephalae* and *Semen cuscutae* at the ratio by weight of 0.1-1:2-20:1-5:0.1-1:0.1-1:0.1-1. The more preferable ratio is 0.5:5:2:0.5:0.25:0.5.

The preferable *Lignum aquilariae resinatum* is the resin containing trunk of *Aquilaria agallocha Roxb.* The preferable *Resina boswelliae carterii* is the gelatinous resin of tree bark of *Boswellia carterii Birdw.*

On the other hands, the present invention concerns a method to prepare the herbal composition including the following processes:

(1). Extracting of *Semen lactucae sativae, Lignum aquilariae resinatum, Fructus oryzae, Resina boswelliae carterii, Rhizoma atractylodis macrocephalae* and *Semen cuscutae* at the aforementioned ratios.

(2). Mixing the effective amount of the extract with pharmaceutically acceptable carriers, excipients or diluents to make into the expecting dosage forms by known prior art.

The dosage forms include, but not limit to, lozenge, tablet, film coated tablet, capsule, soft capsule, granule, powder, pill, solution, emulsion, injection solution, injection, ointment, cream, spray or inhalant.

On the other aspect of the present invention, it provides a method to prevent and to treat bone fracture and osteoporosis by administration of an effective amount of the herbal composition of the present invention. It can be administered via oral, intramuscular, intra-venous, mucosal or topical route, for example, oral administration of tablet, film coated tablet, capsule, soft gel, granules, powder, pill, liquid, emulsion or topical application of ointment or lotion to prevent and to treat bone fracture and osteoporosis.

The biological activities of the present invention including stimulation of bone morphogenetic protein-2 (BMP-2) expression, stimulation of osteoblast proliferation, promotion of bone fracture healing in rabbit, treatment of osteoporosis in ovariectomized rats, analgesic effect in acetic acid induced pain in mice, promotion of locomotor activity in loaded swimming in mice, oral acute toxicity and oral chronic toxicity studies are discussed as below.

As demonstrated in Experiment 1, stimulation of BMP-2 expression by powder A and B of example 1 and 2 of the present invention, 0.3% ground powder A of example 1 increased the expression of BMP-2 by 70.2%; 0.3% of extract powder B of example 2 increased the expression of BMP-2 by 125.5%.

As demonstrated in Experiment 2, stimulation of osteoblast proliferation of the present invention, the extract powder C of example 3 stimulated the proliferation of osteoblasts dose-dependently.

As demonstrated in Experiment 3, promotion of bone fracture healing in rabbits, the pill of example 4 stimulated the healing rate of bone fracture in rabbit. At the early stage of healing, pill of example 4 promoted the removal of blood clot, osteoblast proliferation and differentiation, and trabecular formation. At the middle stage of healing, pill of example 4 promoted the maturation and mineralization of trabeculae and bony callus formation. At the late stage of healing, pill of example 4 promoted the remodeling of bone and reunion of bone marrow canal.

As demonstrated in Experiment 4, treatment and prevention of osteoporosis in ovariectomized rats, the extract powder C of example 3 promoted the bone formation in ovariectomized osteoporotic rats. It stimulated the differentiation of osteoblasts, osteoid formation and mineral apposition. Dosing of example 3 for 70 days, the bone metabolic parameters of trabecular bone volume (TBV), single label of tetracycline signal (STS), double label of tetracycline signal (DTS), bone rebuilt time, and adjusted mineral apposition rate (iMAR) were comparable to those of sham-operated group.

As demonstrated in Experiment 5, analgesic effect of acetic acid induced pain in mice, by orally administering 1.0, 2.0, or 4.0 raw material equivalent/Kg of powder B of example 2, the abdominal contortion numbers decreased significantly. It demonstrated that the present invention has analgesic effect.

As demonstrated in Experiment 6, locomotor activity promotion of loaded swimming in mice, by orally administering 0.5, 1.0, 2.0, or 4.0 raw material equivalent/Kg of powder B of example 2, the swimming time of the weight-loaded mice increased significantly. It demonstrated that the present invention has locomotor activity promotion effect.

As demonstrated in Experiment 7, oral acute toxicity in rats, the body weight and vital signs of the treated group were comparable to those of the control group in both male and female rats during 14 days of observation period. The gross necropsy did not detect any observable lesions in both groups. At the dose of 5000 mg/Kg, the powder C of example 3 did not cause any observable pharmacotoxic effects. The present invention is considered practically non-toxic.

As demonstrated in Experiment 8, oral chronic toxicity in rats, the vital signs, appearance, feces, and food-intake were normal. The body weight, hematology, blood chemistry and the weight index of major organs were not different between the present invention treated group and control group. There were no pathological changes on the histological analysis of major organs including heart, liver, spleen, kidney, bladder, lung, stomach, duodenum, ileum, colon, pancreas, uterus, ovary, testis, epididymis, prostate, brain, pituitary gland, thyroid gland, adrenal gland, thymus, lymph node, and bone marrow in the treated group and control group. At the dose of 106 folds of suggested human use of powder B of example 2 for three months, there were no toxicities detected by the present invention.

In summary of the aforementioned biological data, the present invention is a non-toxic, BMP-2 expression stimulating and osteoblast proliferation stimulating composition. It also demonstrates analgesic and locomotor enhancing effects. The present invention is able to facilitate the healing of bone fracture and to treat osteoporosis. The herbal composition of the present invention is useful in prevention and treatment of bone fracture and osteoporosis.

DETAILED DESCRIPTION OF THE INVENTION

Preparation of the Present Invention

EXAMPLE 1

Preparation of Powder A 2000 g of *Lignum aquilariae resinatum*, 800 g of *Fructus oryzae*, 200 g of *Resina boswelliae carterii*, 200 g of *Semen lactucae sativae*, 100 g of *Rhizoma atractylodis macrocephalae* and 200 g of *Semen cuscutae* were individually ground into powder. The powders were mixed thoroughly and passed through 100 mesh sieve.

EXAMPLE 2

Preparation of Powder B

Step 1. 400 g of *Lignum aquilariae resinatum* and 267 g of *Fructus oryzae* were individually ground into powder and passed through 60 mesh sieve.

Step 2. 533 g of *Fructus oryzae*, 200 g of *Resina boswelliae carterii*, 1600 g of *Lignum aquilariae resinatum*, 200 g of *Semen lactucae sativae*, 100 g of *Rhizoma atractylodis macrocephalae* and 200 g of *Semen cuscutae* were soaked in deionized water and heated to 100° C. for 2.5 hours. The extracted fluid was collected, passed through 100 mesh sieve and rotary evaporated. The concentrated extract fluid was then mixed with the powder from step 1, and made it into granules.

Step 3. The granules were placed in oven at 60° C. for 4 hours until the water content was less than 9%. The dried granules were then passed through 200 mesh sieve.

EXAMPLE 3

Preparation of Powder C 2000 g of *Lignum aquilariae resinatum*, 800 g of *Fructus oryzae*, 200 g of *Resina boswelliae carterii*, 200 g of *Semen lactucae sativae*, 100 g of *Rhizoma atractylodis macrocephalae* and 200 g of *Semen cuscutae* were soaked in deionized water and heated to 100° C. for 2.5 hours. The extracted fluid was collected, passed through 100 mesh sieve, and spray dried into powder.

EXAMPLE 4

Preparation of Pill

The powder prepared by example 1 was mixed with heated honey at 1:1 ratio and made into pills.

EXAMPLE 5

Preparation of Capsule

The powders prepared by example 2 or 3 were mixed with pharmaceutically acceptable excipients, carriers or diluents, sieved and packed into capsules.

EXAMPLE 6

Preparation of Tablet

The powders prepared by example 2 or 3 were mixed with pharmaceutically acceptable excipients, carriers or diluents, sieved and made into tablets. It can also be made into granules by the known pharmaceutical technique and then made into tablets.

EXAMPLE 7

Preparation of Oral Liquid Dosage Form

The powders prepared by example 2 or 3 were mixed with pharmaceutically acceptable emulsion agents and deionized water into oral liquid dosage form.

Biological Activity Assays

The results of the biological studies of the present invention including stimulation of BMP-2 expression, stimulation of osteoblast proliferation, promotion of bone fracture healing in rabbits, treatment and prevention of osteoporosis in ovariectomized rats, analgesic effect of acetic acid induced pain in mice, locomotor activity promotion of loaded swimming in mice, oral acute toxicity and oral chronic toxicity in rats were described in details in the following.

The preparations used in the studies:
(1). Stimulation of BMP-2 expression: powder A was prepared as in example 1, powder B was prepared as in example 2.
(2). Stimulation of osteoblast proliferation: powder C was prepared as in example 3.
(3). Promotion of bone fracture healing in rabbits: pill was prepared as in example 4.
(4). Treatment and prevention of osteoporosis in ovariectomized rats: powder C was prepared as in example 3.
(5). Analgesic effect of acetic acid induced pain in mice: powder B was prepared as in example 2.
(6). Locomotor activity promotion of loaded swimming in mice: powder B was prepared as in example 2.
(7). Oral acute toxicity in rats: powder C was prepared as in example 3.
(8). Oral chronic toxicity in rats: powder B was prepared as in example 2.

Experiment 1

In Vitro Assay: Stimulation of BMP-2 Expression of the Present Invention

References:
Stimulation of bone formation in vitro and in rodents by statins. Science, 1999, 286: 1946-1949. Compactin and simvastatin, but not pravastatin, induce bone morphogenetic protein-2 in human osteosarcoma cells. Biochem. Biophy. Res. Commun., 2000, 271(3): 688-692.

In vitro and in vivo studies of bone morphogenetic protein-2 expressing adenoviral vector. J. Bone Joint Surg. Am., 2001, 83A suppl. 1 (Pt 2): S99-104.

A luciferase reporter vector containing 5'flanking promoter region of BMP-2 gene was constructed and tansfected into osteoblasts. By measuring the fluorescence emitted by the enzymatic activity of luciferase after adding the substrate luciferin, the level of expression of BMP-2 can be determined. The results were shown in Table 1 and 2.

As shown in Table 2, powder A and powder B did not contain luciferase activity. As shown in Table 1, 0.3% powder A increased the expression of BMP-2 70.2%, while 0.3% powder B increased the expression of BMP-2 125.5%.

Experiment 2

In Vitro Assay: Stimulation of Osteoblast Proliferation of the Present Invention Reference:
Menadione-induced cytotoxicity to rat osteoblasts. Cell Mal. Life Sci. 1997, 53: 967-976.

The calvaria of Wistar neonatal rats were serially digested by 0.2% type I collagenase (Sigma) at 37° C. each for 30 minutes. The cells released between digestion 3 to 5 were collected and cultured in Dulbecco's modified eagle medium (DMEM) (Gibco) containing 10% fetal calf serum (FCS), 100 units/ml penicillin G, 100 ug/ml streptomycin in humidifying atmosphere containing 5% $CO_2$ at 37° C.

$1 \times 10^4$ cells were plated in each well of 96 well multiwell plate (Nunc). 48 hours later, 0.1, 1, 10, 100, 1000 ug/ml of powder prepared by example 3 were added. The cells were cultured for a further of 3 days, and 100 ul of the final concentration of 0.5 mg/ml of 3-(4,5-dimethylthiazol-2-yl)-2,5-diphenyltetrazolium bromide (MTT) was added and incubated for 4 hours at 37° C. At the end of incubation, the supernatant was aspirated and 100 ul of isopropanol containing 0.04 N hydrochloric acid was added. The dissolved formazan was measured at 570 nm by an enzyme-linked immunosorbant assay (ELISA) reader.

The percentage of promotion was calculated by the following formula:

Promotion rate=[(preparation added M.O.D.–preparation non-added M.O.D.)/preparation non-added M.O.D.]×100

M.O.D.: mean of optical density, S.D.: standard deviation

As shown in Table 3, the composition of the present invention was able to stimulate the proliferation of osteoblasts at 24 and 72 hours of incubation. The promotion rate of 72 hours was less than that of 24 hours possibly due to the exhaustion of nutrients or accumulation of metabolites.

Experiment 3

In Vivo Assay: Promotion of Bone Fracture Healing in Rabbits

References:
An experimental study of dan sheng improving the mandibular bone fracture healing. Chineese J. Stomatology, 1992, 27(4); 215-216.

Effect of nicotine on the rate and strength of long bone fracture healing. Clin. Orthop. & related Res. 1998, 353: 231-237.

40 rabbits at body weight of 1.5 to 2 Kg, half male and half female, were quarantined for one week. The forearm was dissected under sterile condition after the animals were analgesized. At proximal ⅓ of radius, a 2 mm transverse fracture was created by electric saw. The wound was sutured. The rabbits were grouped into 5, 12, 17, 23, and 30 days. Each group contained 8 rabbits, 5 treated and 3 control. Control was given standard rabbit chow, and treated was given pill as prepared by example 4 in addition to standard rabbit chow at the dose of 2 g example 4, BID. The rabbits were sacrificed at early (5-12 days), mid (17-23 days) and late (23-30 days) stages of healing. X-ray radiography and histopathology were analyzed.

The results were shown as follows:

(a). Body locomotion observation: the experimental group recovered faster than the control group. The forearm of the pill treated group was able to support their body weight earlier than the control group.

(b). X ray radiography: The conditions of healing of fractures in pill treated group were better than the control group at all time intervals studied.

(c). Histopathological observations:

(c-i). 5 days after surgery: In the control group, there were clot and necrosis at the fractured ends; there no significant changes in periosteum and endoosteum. In the pill of the present invention treated group, there were clot and necrosis at the fractured ends; there were invasions of blood vessels; there were proliferation of osteoblasts in periosteum and neo-capillarization in endoosteum.

(c-ii). 12 days after surgery: In the control group, there were some persistent clot and necrosis; some fibrocallus formed; there were some biological activities in periosteum; some hyaline callus formed in limited region. In the pill of the present invention treated group, there was fibrocallus formed at the fractured ends; there was significant neo-osteogenesis in periosteum at the proximal end of fracture; there were also some bony callus formed.

(c-iii). 17 days after surgery: In the control group, there was large amount of hyaline callus; marrow canal was not completely sealed by callus. In the pill of the present invention treated group, there was significant neo-osteogenesis at the fractured ends; mineralization occurred; marrow canal was sealed by callus; there were blood vessels presented.

Figure 1:
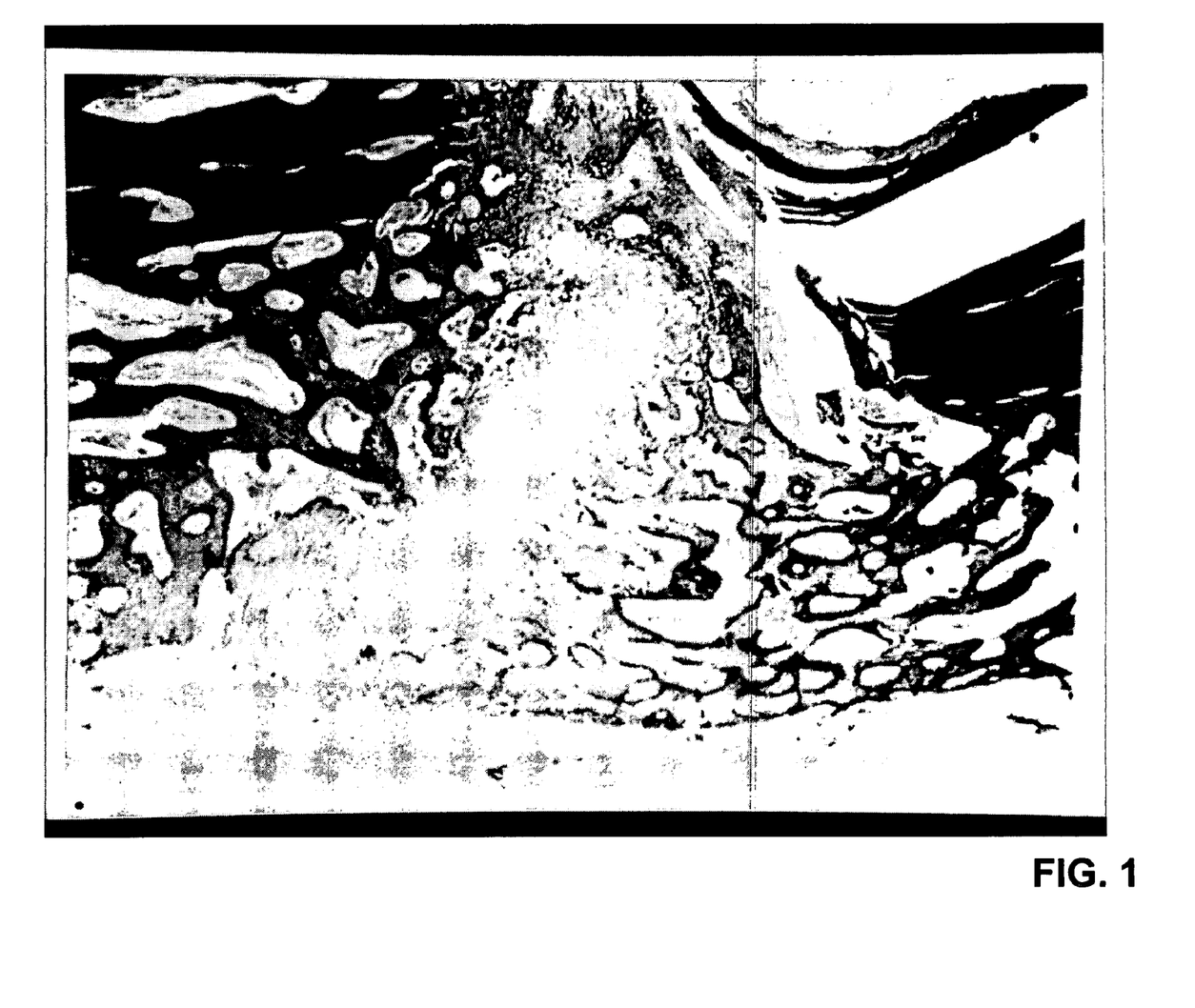
FIG. 1. Bone fracture control group: 23 days after surgery. 40× magnification, Masson stain.
Figure 2:
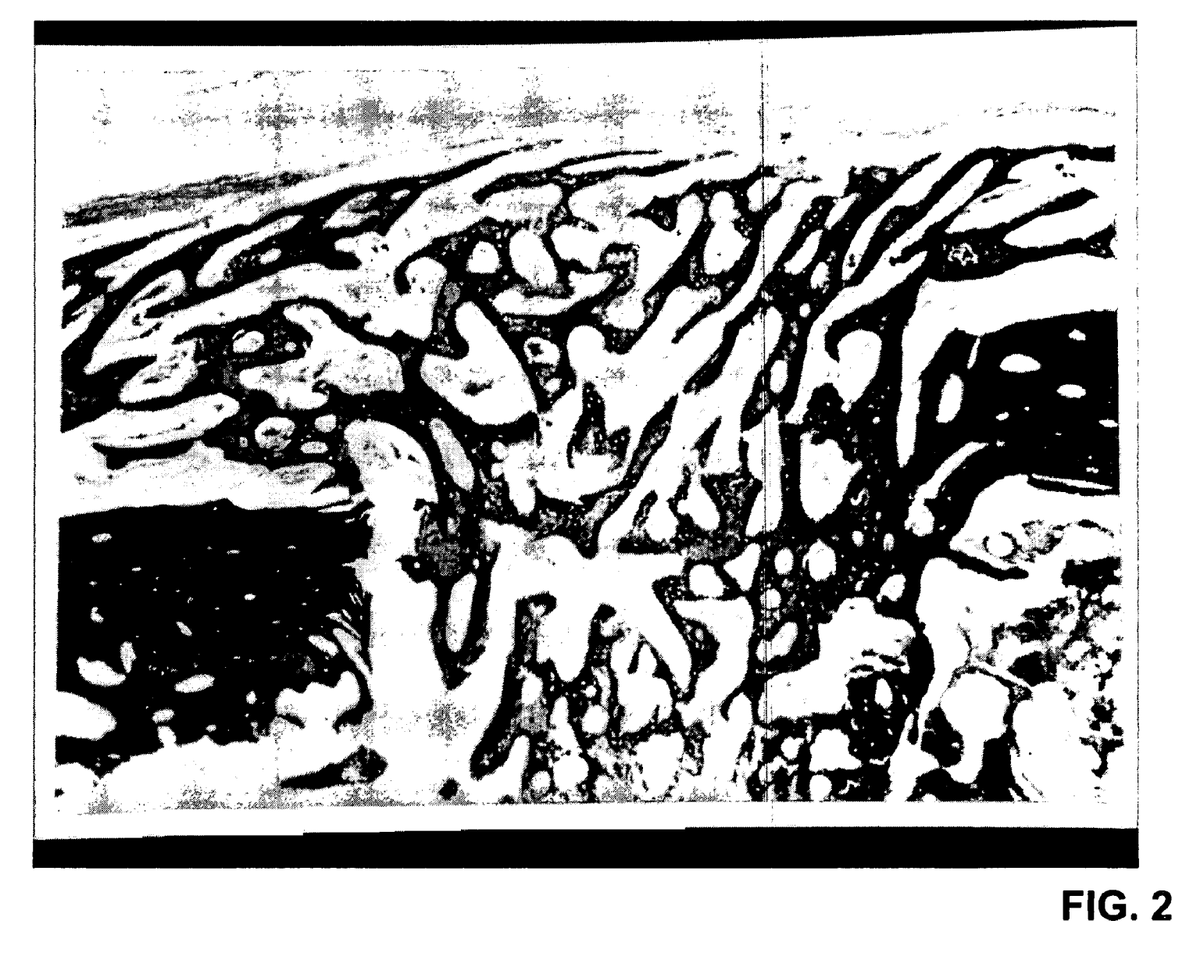
FIG. 2. Bone fracture pearl of example 4 treated group: 23 days after surgery. 40× magnification, Masson stain.

(c-iv). 23 days after surgery: In the control group, there was mostly, but not completely bony callus at the fractured ends, but there was some hyaline callus in the cleft of the fractured ends as shown in FIG. 1. In the pill of the present invention treated group, the fractured ends were completely healed by bony callus. There was significant remodeling on outer bony callus and many blood vessels among trabeculae as shown in FIG. 2. Under higher magnification, the bony callus at the ends of sealed marrow canal showed bone resorption and formation remodeling activities.

Figure 3:
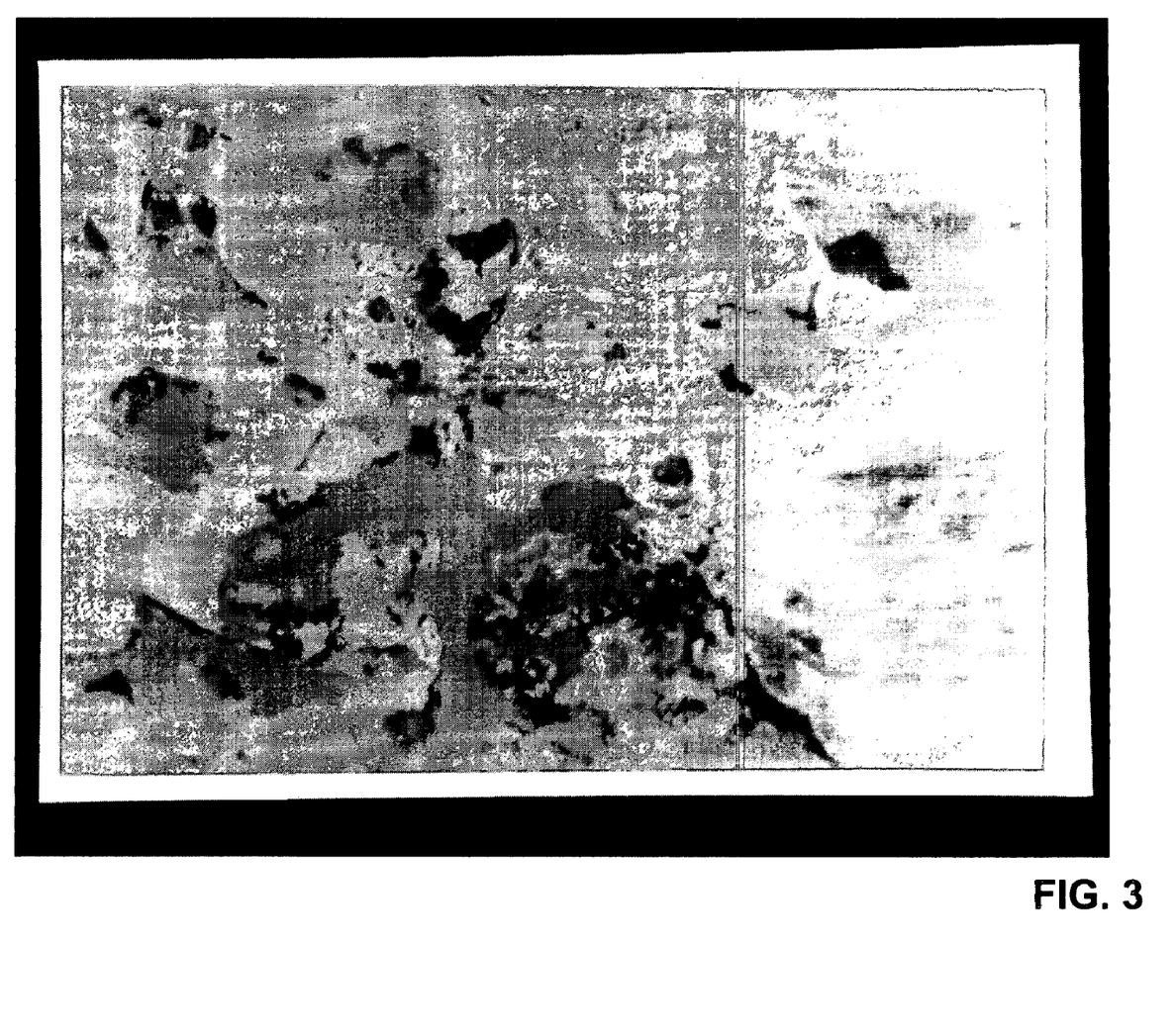
FIG. 3. Bone fracture control group: 30 days after surgery. 100× magnification, Fluoresence stain.
Figure 4:
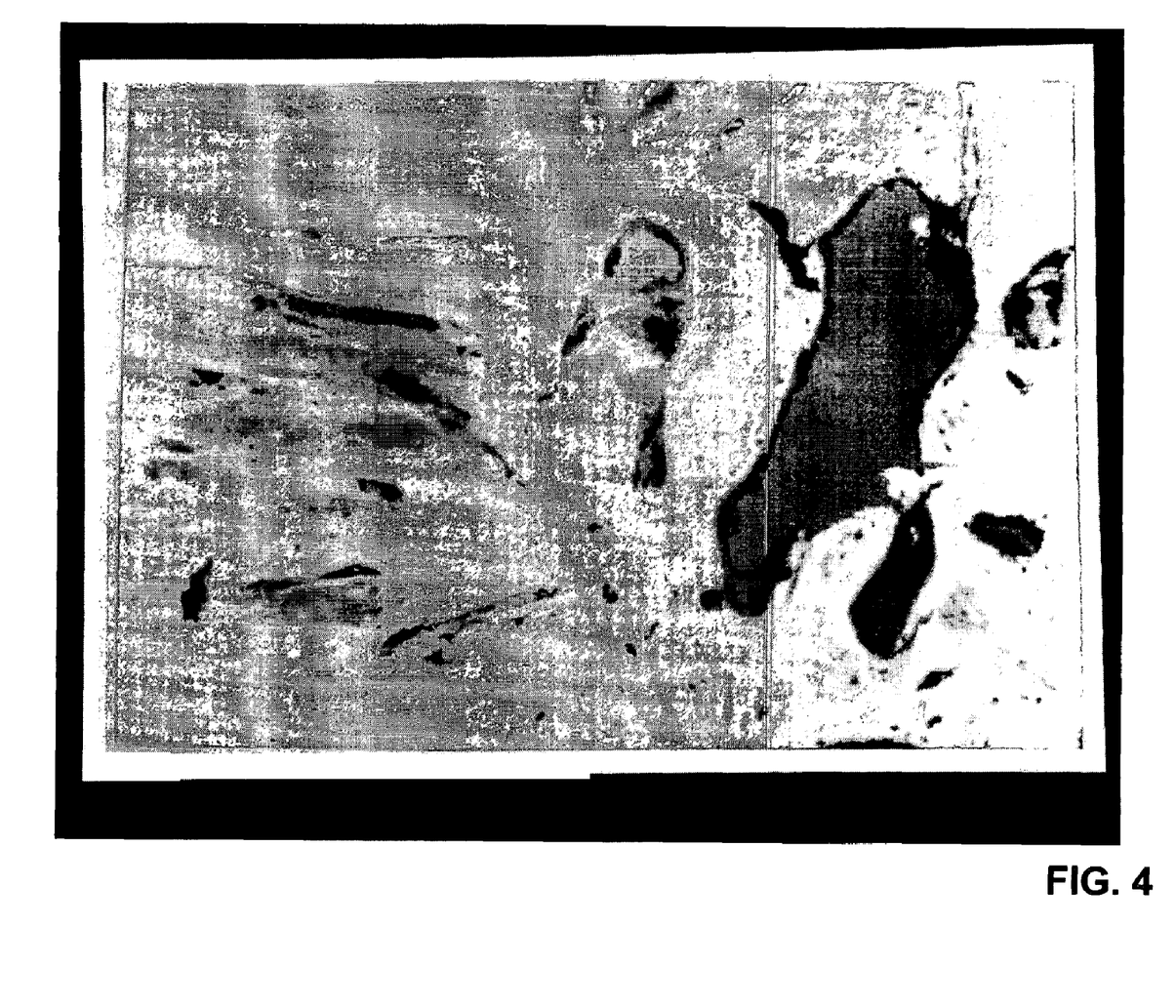
FIG. 4. Bone fracture pearl of example 4 treated group: 30 days after surgery. 100× magnification, Fluoresence stain.

(c-v). 30 days after surgery: As shown in FIG. 4, in the pill of the present invention treated group, the bony callus at the fractured ends was mature; the periosteum of callus and fractured ends was well connected; the epiphyses at the fractured ends showed bone remodeling; tetracycline double label was apparent. It was clinically healed. As shown in FIG. 3, in the control group, the bony callus at the fractured ends was not mature; there was some hyaline calcification; the epiphyses at the fractured ends showed insignificant bone remodeling; callus and fractured ends was not well connected; tetracycline label was mostly single.

In summary of the results, the pill of the present invention treated group showed significant facilitation on healing of bone fracture in rabbit model. At the early stage, the present invention promoted the activation of clot at the fractured ends, stimulated osteoblast proliferation and differentiation, promoted trabecular formation; at the mid stage, the present invention promoted trabecular maturation and mineralization, and bony callus formation; at the late stage, the present invention promoted the bone remodeling, facilitated the reunion of marrow canal.

Experiment 4

In Vivo Assay: Treatment and Prevention of Osteoporosis in Ovariectomized Rats

References:

Effect of ovariectomy and calcium deficiency on the ultrasound velocity, mineral density and strength in the rat femur. Clin. Biomech., 1998, 13(7): 480-484.

The use of estrogen, DHEA, and diosgenin in a sustained delivery setting as a novel treatment approach for osteoporosis in the ovarictomized adult rat model. Biomed. Sci., 2001, 37: 281-286.

Study of nylestriol effect on bone histomorphometric parameters in ovariectomized rats. Zhonghua Fu Chan Ke Za Zhi, 1999, 34(2): 86-89.

52 female Sprague-Dawley rats at the body weight of 200 g were divided into 4 groups: sham-operated control group, ovariectomied group, ovariectomized for 30 days and dosing for the last 40 days group, and ovariectomized for 30 days and dosing for the last 70 days group.

Figure 5:
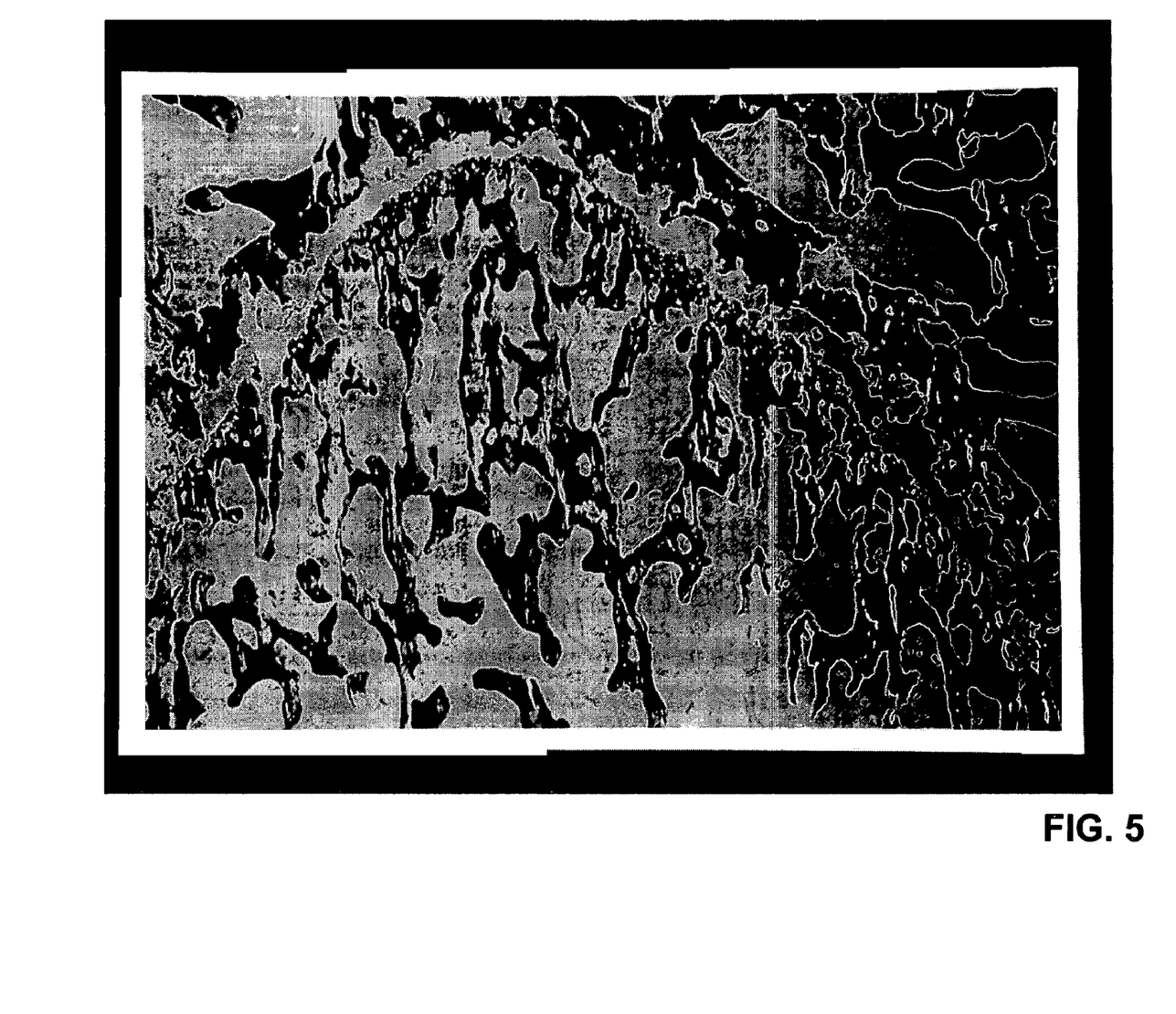
FIG. 5. Osteoporosis/ovariectomy sham-operation control group: 30 days after sham-operation. 40× magnification, von Kossa stain.
Figure 6:
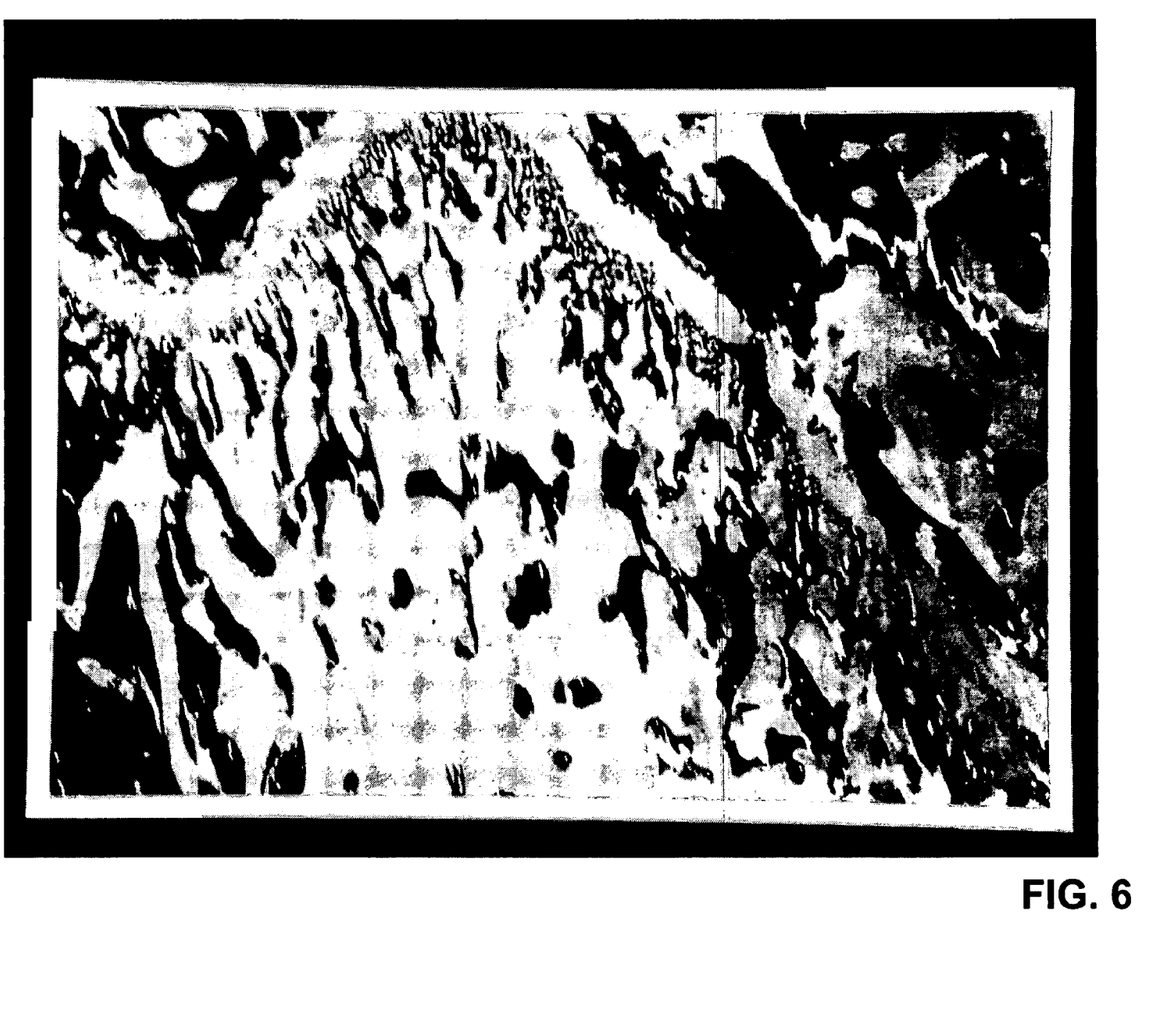
FIG. 6. Osteoporosis/ovariectomy group: 30 days after ovariectomy. 40× magnification, von Kossa stain.

(4-a). Ovariectomy:

Rats were ovariectomized or sham-operated under analgesia. One month later, 5 rats of each group were sacrificed to observe if osteoporosis was established. The results showed that in sham-operated group, the structure of trabeculae underneath the epiphyses of distal end of femur was mature, dense, and even in thickness as shown in FIG. 5. In group of ovariectomy for 30 days, the structure of trabeculae underneath the epiphyses of distal end of femur was not mature, the connections among trabeculae were poor, and there were many blind-ends of trabeculae and osteoid on the surface of trabeculae. This demonstrated osteoporosis with high activities of bone rebuilt and bone turn-over as shown in FIG. 6. There was significant difference in the structure of trabeculae between sham-operated control and ovariectomized rats.

(4-b). Dosing after 30 days of ovariectomy:

30 days after ovariectomy, the rats were orally given 0.12 g of powder C (prepared as in Example 3) per day. 40 days later, 4 rats in each of the 4 groups were sacrificed, and histological sections were prepared and observed. The surviving rats were further dosing for 30 days and sacrificed at the end of experiment. Bone mineral density (BMD), pathohistology, bone histomorphometry were performed and analyzed.

(4-c). BMD measurement

The BMD of the right femur of the rats were measured by Hologic QDR-4500W(S/N 47192).

(4-d). Bone histomorphometry

Sections of trabeculae at 1 cm underneath epiphyses were selected. Three pictures were selected from areas that were divided into endo-, meso- and epi-regions, and scanned and analyzed by computer equipped with MPLAS-500. Each sample was stained with Gemisa for histology, von Kossa for osteoid and tetracycline for fluorescence observation. Histomorphometry study included trabecular bone volume (TBV), single tetracycline signal (STS), double tetracycline signal (DTS), STS/DTS ratio, trabecular osteoid surface (TOS), mean osteoid surface width (MOSW), mineralization time, bone rebuilt time, bone surface, bone resorption surface, mineral apposition rate (MAR), adjusted mineral apposition rate (iMAR).

(4-e). The results of the experiment were described as follows:

(4-e-i). Dosing for 40 days after 30 days of ovariectomy:

In ovariectomized group (70 days after ovariectomy), the architecture of trabeculae underneath epiphyses of distal femur end were even more porous, thin and irregular. The osteoid on the trabecular surface was apparent and bone formation and rebuild were active. It was a typical high bone turn-over osteoporosis phenotype. Dosing for 40 days, although not recovered to the levels of sham-operated control, compared to ovaricetomized group, the density and connection of trabeculae were significantly increased.

Figure 7:
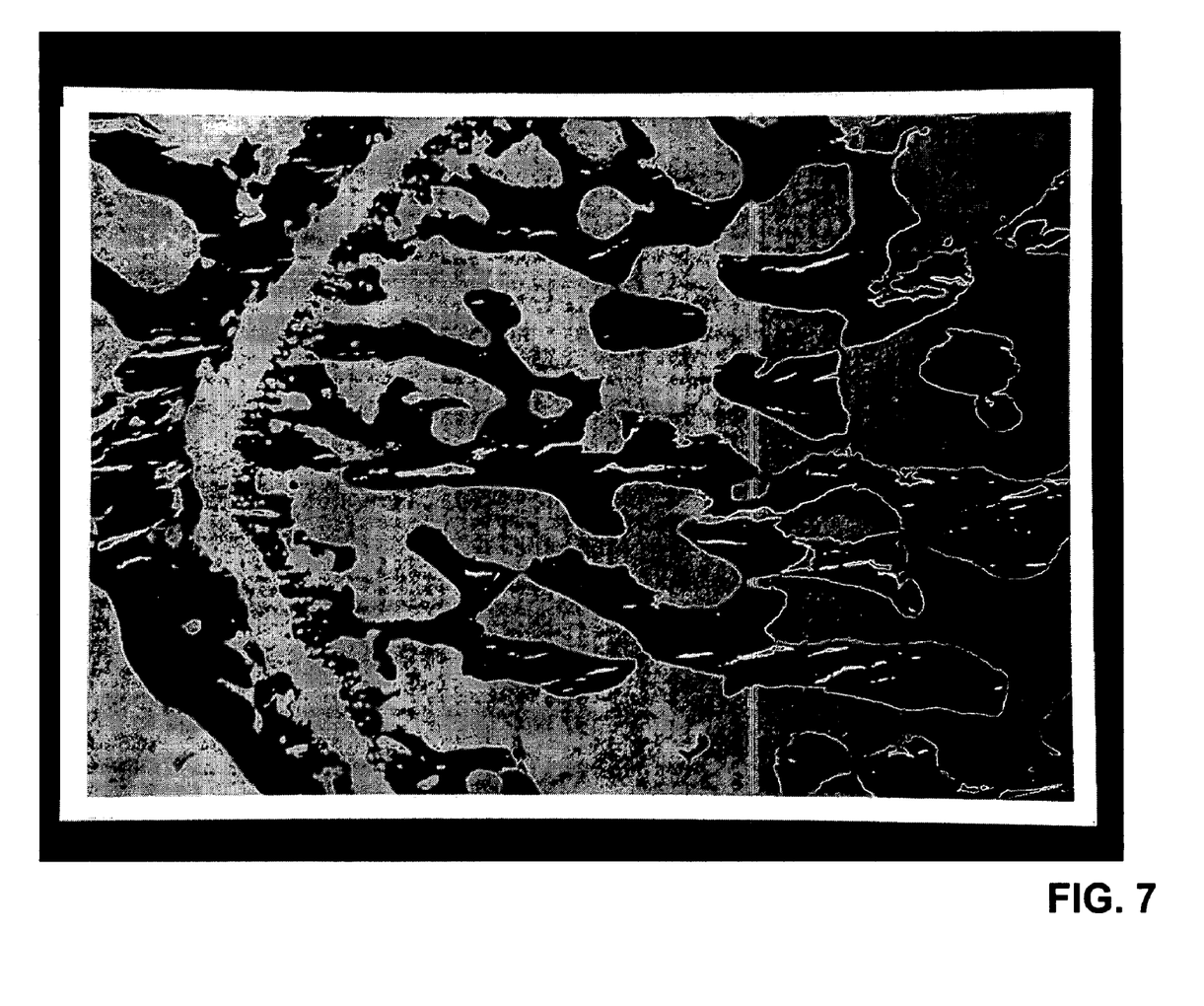
FIG. 7. Osteoporosis/ovariectomy sham-operation control group: 100 days after sham-operation. Structure of trabeculae underneath epiphyses at the distal end of femur.
Figure 8:
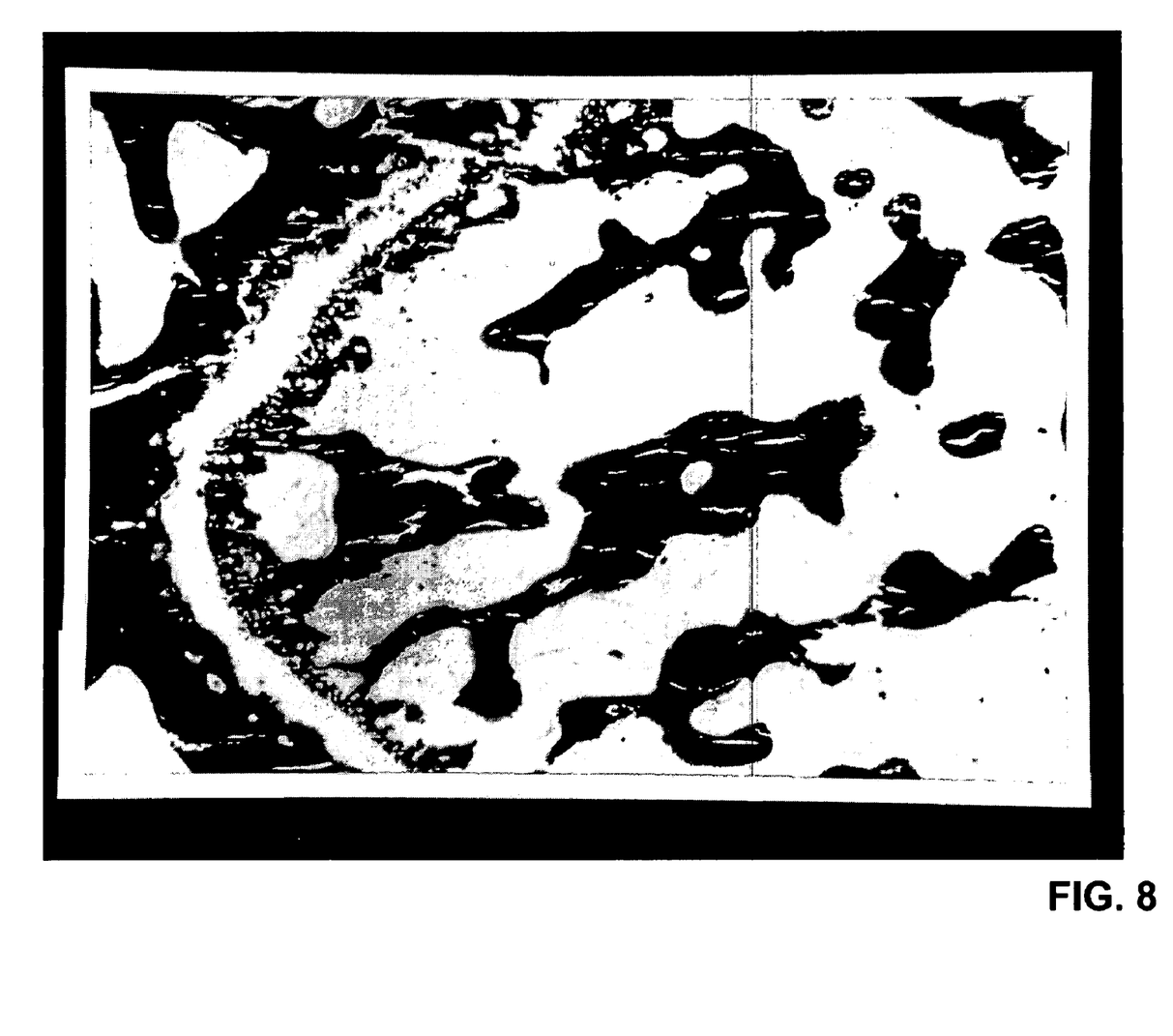
FIG. 8. Osteoporosis/ovariectomy group: 100 days after ovariectomy. Structure of trabeculae underneath epiphyses at the distal end of femur.

(4-e-ii). Dosing for 70 days after 30 days of ovariectomy:

In sham-operated group, the architecture of trabeculae underneath epiphyses of distal femur end were mature, dense, even in thickness as shown in FIG. 7. In ovariectomized group (100 days after ovariectomy), the architecture of trabeculae underneath epiphyses of distal femur end were highly porous, thin and irregular in thickness, many blind ends of trabeculae and with high amount of osteoid on trabecular surfaces. This was a high bone turn-over osteoporosis phenotype as shown in FIG. 8.

Figure 9:
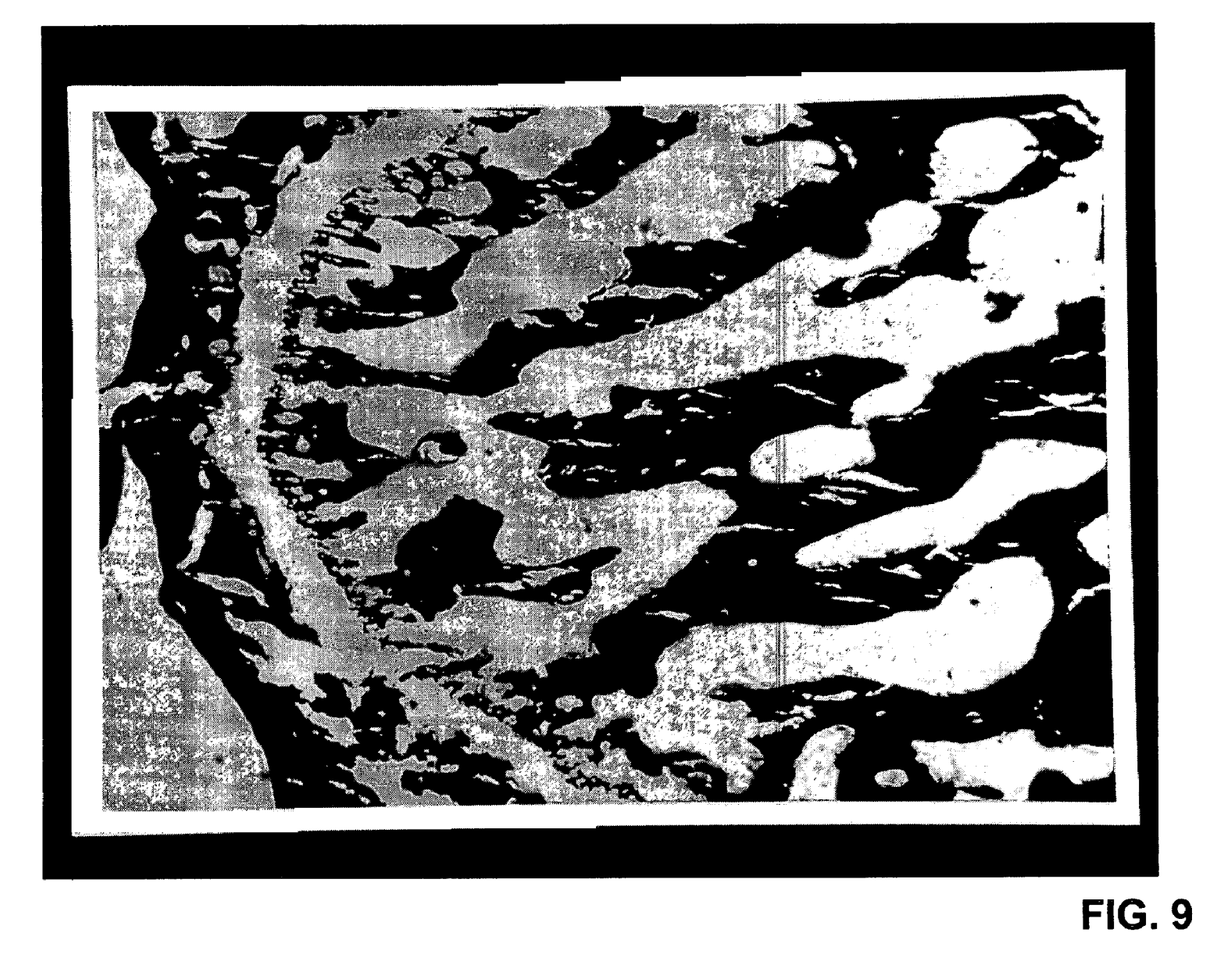
FIG. 9. Osteoporosis/ovariectomy-powder C treated for 70 days group: 100 days after ovariectomy and dosing for the last 70 days. Structure of trabeculae underneath epiphyses at the distal end of femur.

As shown in FIG. 9, dosing for 70 days after 30 days of ovariectomy, the architecture of trabeculae underneath epiphyses of distal femur end was comparable to that of sham-operated control. The trabeculae were interwoven into web with dense and even thickness. The osteoid on trabecular surfaces was similar to that of the control. The bone rebuilding was not as active as in ovariectomized group.

(4-e-iii). As shown in Table 4, femur BMD of the group of dosing for 70 days was recovered to the level of the sham-operated control.

(4-e-iv). Histomorphometry:

As shown in Table 5, the effects of the present invention on histomorphometry of oeteoporosis were summarized as follows:

TBV: Dosing for 70 days after 30 days of ovarictomy, TBV was recovered to that of sham-operated group.

STS: Dosing for 70 days after 30 days of ovariectomy, STS was recovered to that of sham-operated group.

DTS: Dosing for 70 days after 30 days of ovariectomy, DTS was recovered to that of sham-operated group.

STS/DTS ratio: STS/DTS ratio was not significantly different among three groups.

TOS: TOS was higher in ovariectomized group than in sham-operated group; TOS in group of dosing for 70 days after 30 days of ovarictomy was higher than in sham-operated group, and was similar to that in ovariectomized group.

MOSW: MOSW in ovariectomized group and dosing for 70 days after 30 days of ovariectomy group was significantly wider than that in sham-operated group.

Mineralization time: There were no significant differences among three groups.

Bone rebuilt time: Bone rebuilt time of groups of sham-operated and dosing for 70 days after 30 days of ovarictomy was significantly longer than that of ovariectomized group.

Bone surface: Bone surface of groups of ovariectomy and dosing for 70 days after 30 days of ovarictomy was significantly bigger than that of sham-operated group.

Bone resorption surface: Bone resorption surface of groups of ovariectomy and dosing for 70 days after 30 days of ovarictomy was significantly bigger than that of sham-operated group. Bone resorption surface of group of dosing for 70 days after 30 days of ovarictomy was significantly bigger than that of ovariectomized group.

MAR: MAR of groups of ovariectomy and dosing for 70 days after 30 days of ovarictomy was faster than that of sham-operated group. MAR of ovariectomized group was faster than that of dosing for 70 days after 30 days of ovarictomy group.

iMAR: iMAR of dosing for 70 days after 30 days of ovarictomy group was slower than that of ovariectomized group, and recovered to the rate of that of sham-operated group.

It was clearly shown that the herbal composition of the present invention was able to activate bone formation and bone resorption. The herbal composition of the present invention stimulated osteoblast formation, and osteoid and mineral deposition in matrix. The bone metabolic parameters, TBV, STS, DTS, bone rebuilt time, and iMAR, were recovered to the levels of sham-operated control after dosing of powder C of the present invention for 70 days after 30 days of ovarictomy.

Experiment 5

In Vivo Assay: Analgesic Effect of Acetic Acid Induced Pain in Mice

References:

Peripheral and preemptive opioid antinociception in a mouse visceral pain model. Pain, 2001, 89(2-3): 221-227.

Preliminary studies on the analgesic activity of latex of *Calotropris procera*. J. Ethnopharmacol. 2000, 73(1-2): 307-311.

Studies on the anti-inflammatory and related pharmacological properties of the aqueous extract of *Bridelia ferruginea* stem bark. J. Ethnopharmacol. 2000, 71(1-2): 153-160.

72 mice of Quen-ming strain with body weight of 18-22 g, half male and half female, were randomized into 6 groups. They were fast overnight, then, were given saline, 0.2 g/Kg of aspirin, or raw material equivalent of 0.5, 1.0, 2.0, 4.0 g (equivalent to 0.06, 0.12, 0.24, 0.48 g of powder B, respectively)/Kg of body weight (prepared as in Example 2).

One hour after dosing, the mice were intra-peritoneally injected with 0.2 ml of 0.3% acetic acid. The abdominal contortion numbers in 20 minutes were recorded as the measurement of analgesic effect.

The results were shown in Table 6. The present invention showed significant analgesic effect in acetic acid induced abdominal contortion in mice. At raw material equivalent of 1.0, 2.0, 4.0 g/Kg of powder B, there were significant decreases in numbers of abdominal contortion. At raw material equivalent of 0.5 g/Kg of powder B decreased the number of abdominal contortion, but not statistically significant. It indicated that powder C of the present invention had pain relief activity.

Experiment 6

In Vivo Assay: Locomotor Activity Promotion of Loaded Swimming in Mice

References:

The effect of swimming on bone remodeling and composition in young adult rats. Calcif. Tissue Int., 1990, 47(3): 173-177.

Effects of exposure to hypobaric-hypoxia on body weight, muscular and hematological characteristics, and work performance in rats. Jpn. J. Physiol., 1997, 47(1): 51-57.

Pharmacological study on *Agkistrodon blomhoffii* BOIE. V. Anti-fatigue effect of the 50% ethanol extract in acute weight-loaded forced swimming-treated rats. Biol. Pharm. Bull., 1996, 19(1): 62-66.

72 mice of Quen-ming strain with body weight of 18-22 g, half male and half female, were randomized into 6 groups. They were fast overnight, then, were given saline, 3 g/Kg of Ku-Su-Kun, and raw material equivalent of 0.5, 1.0, 2.0, 4.0 g (equivalent to 0.06, 0.12, 0.24, 0.48 g of powder B, respectively)/Kg of body weight (prepared as in Example 2) for consecutive three days. Ku-Su-Kun was an approved herbal combination for treatment of osteoporosis in China. Ku-Su-Kun is composed of *Epimedii Herba, Rehmanniae Preparata Radix, Astragali Radix, Salviae Miltiorrhizae Radix, Rhizoma Drynariae.*

One hour after the last dosing, a 2 g of weight was loaded to the tail of the mice. The mice were then placed in a water tank with water of 15 cm in depth at 25° C. The swimming exhaustion time was measured starting from the noses of the mice were submerged underneath the water surface for 10 seconds.

The results were shown in Table 7. The powder B of the present invention showed significant promotion on locomotor activity. At the doses of raw material equivalent of 0.5, 1.0, 2.0, 4.0 g/Kg of powder B, the time to exhaustion was significantly increased compared to saline control. It indicated that the powder B of the present invention increased locomotor activity and had anti-fatigue effect.

Experiment 7

In Vivo Assay: Oral Acute Toxicity in Rats

24 Spraque-Dawley rats with body weight of 200 g, half male and half female, were randomized by LIMS into 2 groups. One group was the vehicle control, the other group was the present invention of powder C (prepared as in Example 3) treated group. Powder C was prepared as aqueous suspension to the concentration of 250 mg/ml in 1% carboxymethyl cellulose (CMC). 10 ml/Kg of the present invention powder C suspension (treatment group) or 1% CMC (control group) was gavaged twice in 2 hours apart in one day. The rats were observed twice daily on mortality, morbidity, and clinical signs for 14 days. Body weight was measured once per week.

Results were shown in Table 8. All of the rats survived. During the 14 day observation period, there were no clinically detectable treatment-related toxicities shown. The body weights in both male and female rats in treated group were comparable to those of the control. At necropsy, there were no gross lesions in organs and tissues in both groups. At the dose of 5000 mg/Kg of the present invention, there was no treatment related toxicity. The present invention was considered "practically non-toxic" according to Loomis (Loomis T A. Essentials of Toxicology. Philadelphia: Lea & Febiger, 1978).

Experiment 8

In Vivo Assay: Oral Chronic Toxicity in Rats 6 to 8 weeks old Wistar rats (provided by Research Center of Laboratory Animals, China Medical Institute, certificate: SCXR1100-0006) with the body weight of 80 to 100 g, half male and half female, were quarantined for one week.

Methods:

(a). Vehicle control group: 1% CMC.

(b). Powder B of the present invention treated group: 16 g raw material equivalent (equivalent to 1.92 g of powder B)/Kg body weight.

Powder B (prepared as in Example 2) of the present invention was prepared in 1% CMC at the concentration of 1.333 g raw material equivalent/ml. 1.2 ml/100 g body weight was gavaged once daily, 6 days a week for a consecutive 3 months.

(c). Animals: The rats were randomized into two groups according to body weight and sex. Water and feed were supplied ad libitum. The body weight and feed were measured once a week. At the end of three months, the rats were sacrificed. The blood was collected for hematology and blood chemistry analysis. The organs were weighed and prepared for histopathological study.

Results:

(1). General Vital Sign Observation:

During the period to experiment, the activity, the appearance, feces and food intake of the rats were normal.

Body weight change of male rats: the body weight of vehicle control group increased from 121±2.2 g (week 0) to 365±20.0 g (week 12); powder B of the present invention treated group increased from 123±2.7 g (week 0) to 357.5±23.3 g (week 12).

Body weight change of female rats: the body weight of vehicle control group increased from 119±4.2 g (week 0) to 231±16.4 g (week 12); powder B of the present invention treated group increased from 117±2.7 g (week 0) to 220±10.8 g (week 12).

There were no significant differences in body weight changes between control and powder B of the present invention treated groups.

(2). Hematology:

As shown in Table 9, there were no significant differences between the control and powder B of the present invention treated groups on Hb, RBC, WBC, PLT, and CT.

(3). Blood Chemistry:

As shown in Table 9, there were no significant differences between the control and powder B of the present invention treated groups on all the parameters in blood chemistries.

(4). Effect on Organ Index of Rats:

All the rats were sacrificed at the end of three months. The wet weights of the organs were measured. The wet weights were divided by body weights to obtain the organ weight index that was expressed as wet weight (g) per 100 g of body weight. As shown in Table 9, there was no significant difference between the control and powder B of the present invention treated groups on organ weight index.

(5). Organ Histopathological Examinations:

The rats were sacrificed after dosing for three months. Major organs including heart, liver, spleen, kidney, bladder, lung, stomach, duodenum, ileum, colon, pancreas, uterus, ovary, testis, epididymis, prostate, brain, pituitary gland, thyroid gland, adrenal gland, thymus, lymph node, and bone marrow were collected and prepared for histopathological examinations. There were no significant differences between the control and powder B of the present invention treated groups on histologies of the organs examined.

By orally administering 16 g raw material equivalent of powder B of example 2 for three months, the general vital signs, hematology, blood chemistry and histopathological examinations of the major organs demonstrated that all the parameters studied showed no sign of drug related toxicity. This dosage was equivalent to 106 folds of suggested human use.

In summary of the aforementioned biological assays, it is concluded that he present invention is a non-toxic herbal composition. It can stimulate BMP-2 expression and osteoblast proliferation in vitro. In vivo, the present invention has analgesic effect and locomotor activation effect. It can also facilitate bone fracture healing and treat osteoporosis. The present invention is useful for preventing and treating bone fracture and osteoporosis.

TABLE 1

Effects on Bone Morphogenetic Protein 2 (BMP-2) Promotor Activity

| Transfection Activity | Drug Conc. (W/V %) | Luciferase Activity (fluorescence unit/ $5 \times 10^5$ cells) | Increase in (%) |
|---|---|---|---|
| PGL3 basic vector | 0 | 15 (a) | — |
| PGL3 BMP2 vector | 0 | 94 (b) | — |
| PGL3 BMP2 vector + Powder A | 0.1 | 90 (c) | 0 |
| PGL3 BMP2 vector + Powder A 70.2 | 0.3 | 160 (d) | |
| PGL3 BMP2 vector + Powder B 125.5 | 0.3 | 212 (e) | |

Note:
1. Transfection: Lipofectin mediated transient transfection
2. Powder A and B: A prepared as in example 1, B prepared as in example 2.
3. Transfection host cells: osteoblast
4. Luminometer: TR717 microplate luminometer, TROPLEX
5. pGL3 basic vector: luciferase reporter plasmid, Promega, Madison, WI
6. Increase in activity (%): $(d - b)/b \times 100 = (160 - 94)/94 \times 100 = 70.2\%$
Increase in activity (%): $(e - b)/b \times 100 = (212 - 94)/94 \times 100 = 125.5\%$

TABLE 2

Measurement of Luminescent Materials and Luciferase Activity

| Test Condition | Drug Conc. (%) | Luciferase Activity (Fluorescence unit/ 100 ul medium) |
|---|---|---|
| Powder A + medium | 0.3 | −1 |
| Powder B + medium | 0.3 | 0 |
| Powder A + medium + luciferase substrate | 0.3 | 2 |
| Powder B + medium + luciferase substrate | 0.3 | 0 |

Note:
1. Medium: Dulbecco's modified eagle medium (DMEM) (Hyclone)
2. Luciferase substrate: Luciferin

TABLE 3

Effect on Promotion of Osteoblast Proliferation

| | 24 hour incubation | | | 72 hour incubation | | |
|---|---|---|---|---|---|---|
| Drug Conc. (ug/ml) | M.O.D. | S.D. | Promotion (%) | M.O.D. | S.D. | Promotion (%) |
| 0 | 0.266 | 0.035 | — | 0.256 | 0.02 | — |
| 0.1 | 0.300 | 0.024 | 12.7 | 0.288 | 0.047 | 12.5 |
| 1 | 0.337 | 0.033 | 26.8 | 0.310 | 0.042 | 21.0 |
| 10 | 0.357 | 0.026 | 34.1 | 0.338 | 0.036 | 37.8 |
| 100 | 0.394 | 0.025 | 48.3 | 0.365 | 0.019 | 42.3 |
| 1000 | 0.531 | 0.042 | 99.7 | 0.380 | 0.037 | 48.2 |

TABLE 4

BMD of Right Femur Bone of Rats (Dosing for 70 days)

| Treatment | Number | Est.Area Est(cm$^2$). | BMC(g) | BMD(g/cm$^2$) |
|---|---|---|---|---|
| Control | 10 | 1.159 ± 0.063 | 0.041 ± 0.013 | 0.034 ± 0.009 |
| Ovariectomy (O) | 10 | 1.131 ± 0.056 | 0.027 ± 0.008 | 0.024 ± 0.005* |
| O + Dosing for 70 days | 10 | 1.126 ± 0.026 | 0.038 ± 0.011** | 0.034 ± 0.008*** |

*Ovariectomy compared with sham-operated control, $p < 0.01$
**The composition of the present invention treated for 70 days compared with ovariectomy, $p < 0.05$
***The composition of the present invention treated for 70 days compared with ovariectomy, $p < 0.01$

TABLE 5

Comparison of Histomorphometry of Control, Ovariectomy, Ovariectomy and Dosing for 70 days

| Group | Sham-operated control | Ovariectomy | Ovariectomy and Dosing 70 days |
|---|---|---|---|
| Number of sample | 10 | 10 | 10 |
| TBV % | 63.3 ± 3.1 | 34.0 ± 2.9** | 61.9 ± 2.9## |
| STS % | 42.7 ± 5.3 | 54.3 ± 9.2* | 41.2 ± 6.7# |
| DTS % | 21.2 ± 4.6 | 28.1 ± 5.0 | 19.4 ± 3.8## |
| STS/DTS % | 48.2 ± 7.0 | 52.3 ± 9.4 | 48.2 ± 12.2 |
| TOS (%) | 30.8 ± 5.4 | 53.3 ± 4.3** | 47.4 ± 5.8 |
| MOSW (um) | 9.6 ± 1.2 | 12.9 ± 1.3** | 11.3 ± 0.7# |
| Mineralization time (days) | .4 ± 2.4 | 5.2 ± 1.2 | 5.9 ± 0.9 |
| Bone rebuild time (days) | 13.8 ± 1.8 | 8.3 ± 1.4** | 15.0 ± 2.9## |
| Bone surface (%) | 47.4 ± 4.1 | 52.4 ± 4.1* | 53.8 ± 4.1 |
| Bone resorption (%) | 17.2 ± 3.5 | 22.5 ± 2.8** | 26.0 ± 2.4# |
| MAR (um/d) | 1.4 ± 0.2 | 2.7 ± 0.5** | 1.9 ± 0.3## |
| iMAR surface (um/d) | 1.9 ± 0.7 | 2.7 ± 0.5* | 1.9 ± 0.6# |

*Ovariectomy compared to sham-operated control, $p < 0.01$
**Ovariectomy compared to sham-operated control, $p < 0.001$
Ovariectomy and dosing 70 days compared to ovariectomy, $p < 0.01$
Ovariectomy and dosing 70 days compared to ovariectomy, $p < 0.001$

TABLE 6

Analgesic Effect in Acetic Acid Induced Abdominal Contortion in Mice (Mean ± SD, n = 12)

| Group | Dose (g/Kg) | Number of abdominal contortion |
|---|---|---|
| Normal saline | — | 24 ± 10 |
| Aspirin | 0.2 | 5 ± 3** |
| The powder B of the present invention | 0.5 | 20 ± 10 |
| The powder B of the present invention | 1.0 | 11 ± 9* |

TABLE 6-continued

Analgesic Effect in Acetic Acid Induced Abdominal Contortion in Mice (Mean ± SD, n = 12)

| Group | Dose (g/Kg) | Number of abdominal contortion |
|---|---|---|
| The powder B of the present invention | 2.0 | 15 ± 9* |
| The powder B of the present invention | 4.0 | 9 ± 8** |

*Compared to normal saline group, $P < 0.05$
**Compared to normal saline group, $P < 0.01$

TABLE 7

Locomotor Effect on Duration of Loaded Swimming to Exhaustion in Mice (Mean ± SD, n = 12)

| Group | Dose (g/Kg) | Duration of swimming to exhaustion (min) |
|---|---|---|
| Normal saline | — | 3.31 ± 1.41 |
| Ku-Su-Kun | 2.5 | 5.02 ± 1.42** |
| The powder B of the present invention | 0.5 | 6.33 ± 3.10** |
| The powder B of the present invention | 1.0 | 4.75 ± 1.53* |
| The powder B of the present invention | 2.0 | 9.70 ± 9.99* |
| The powder B of the present invention | 4.0 | 14.54 ± 15.77** |

*Compared to normal saline group, $P < 0.05$
**Compared to normal saline group, $P < 0.01$

TABLE 8

Oral Acute Toxicity Study in Rats - Mortality, Clinical Signs and Gross Necropsy

| Sex | Dose (mg/Kg) | Mortality (N/N) | Clinical signs | Gross necropsy findings |
|---|---|---|---|---|
| Male | 0 (vehicle control) | 0/6 | No | NOL |
|  | 5000 | 0/6 | No | NOL |
| Female | 0 (vehicle control) | 0/6 | No | NOL |
|  | 5000 | 0/6 | No | NOL |

N/N: number of rats found dead/number of rats observed.
No: not observed.
NOL: no observable lesions were found.

TABLE 9

Oral Chronic Toxicity Study in Rats - Blood, Blood Chemistry and Organ Weight Index (Mean ± SD)

| Item | Male Control | Male Treated | Female Control | Female Treated |
|---|---|---|---|---|
| Hematology | | | | |
| Hb (g/L) | 142.0 ± 7.62 | 140.3 ± 7.63 | 128.8 ± 6.53 | 127.5 ± 8.18 |
| RBC ($\times 10^{12}$/L) | 7.90 ± 0.53 | 8.22 ± 0.28 | 7.70 ± 0.74 | 7.90 ± 0.86 |
| WBC ($\times 10^{9}$/L) | 8.36 ± 1.24 | 8.00 ± 1.64 | 5.78 ± 1.00 | 6.50 ± 1.88 |
| PLT ($\times 10^{9}$/L) | 201.4 ± 43.08 | 169.0 ± 30.0 | 186.8 ± 68.43 | 188.3 ± 14.97 |
| CT (sec) | 63.0 ± 12.5 | 66.0 ± 11.7 | 80.0 ± 13.0 | 74.0 ± 12.6 |
| Blood Chemistry | | | | |
| AST (U/L) | 118.2 ± 29.53 | 133.0 ± 17.22 | 115.8 ± 21.23 | 159.0 ± 63.53 |
| ALT (U/L) | 35.60 ± 7.89 | 40.25 ± 10.90 | 33.00 ± 11.75 | 37.25 ± 7.27 |
| ALP (IU/L) | 48.00 ± 10.56 | 39.50 ± 3.11 | 20.80 ± 9.96 | 17.25 ± 7.27 |
| BUN (mmol/L) | 5.57 ± 0.46 | 5.32 ± 0.71 | 6.49 ± 0.68 | 6.16 ± 0.42 |
| TP (g/L) | 66.18 ± 1.38 | 64.60 ± 2.71 | 74.12 ± 2.89 | 71.07 ± 3.31 |
| ALB (g/L) | 31.30 ± 1.18 | 30.68 ± 0.89 | 37.08 ± 0.89 | 35.77 ± 0.82 |
| BGLU (mmol/L) | 5.98 ± 0.46 | 5.87 ± 0.36 | 6.26 ± 0.39 | 6.68 ± 0.44 |
| T-BIL (μmol/L) | 1.63 ± 0.15 | 1.53 ± 0.19 | 1.68 ± 0.31 | 1.63 ± 0.10 |
| C (μmol/L) | 85.38 ± 9.49 | 78.43 ± 3.01 | 86.00 ± 3.09 | 84.95 ± 6.31 |
| T-CHO (mmol/L) | 1.93 ± 0.21 | 1.62 ± 0.29 | 1.69 ± 0.36 | 1.50 ± 0.33 |
| Organ Weight Index | | | | |
| Heart | 0.33 ± 0.064 | 0.28 ± 0.011 | 0.33 ± 0.033 | 0.34 ± 0.028 |
| Liver | 2.69 ± 0.37 | 2.81 ± 0.19 | 2.58 ± 1.57 | 2.95 ± 0.300 |
| Spleen | 0.17 ± 0.037 | 0.24 ± 0.074 | 0.23 ± 0.016 | 0.24 ± 0.030 |
| Lung | 0.65 ± 0.12 | 0.51 ± 0.11 | 0.54 ± 0.054 | 0.58 ± 0.060 |
| Kidney | 0.62 ± 0.089 | 0.61 ± 0.045 | 0.64 ± 0.030 | 0.70 ± 0.065 |
| Brain | 0.48 ± 0.035 | 0.46 ± 0.057 | 0.68 ± 0.056 | 0.73 ± 0.046 |
| Adrenal gland | 0.020 ± 0.007 | 0.013 ± 0.002 | 0.034 ± 0.009 | 0.040 ± 0.005 |
| Thyroid gland | 0.0065 ± 0.002 | 0.0052 ± 0.001 | 0.010 ± 0.002 | 0.012 ± 0.004 |
| Thymus | 0.096 ± 0.021 | 0.090 ± 0.010 | 0.13 ± 0.029 | 0.12 ± 0.022 |
| Testis | 0.98 ± 0.15 | 0.99 ± 0.047 | | |
| Prostate gland | 0.13 ± 0.031 | 0.11 ± 0.028 | | |
| Uterus | | | 0.29 ± 0.049 | 0.26 ± 0.089 |
| Ovary | | | 0.094 ± 0.023 | 0.091 ± 0.011 |

What is claimed is:

1. A pharmaceutical composition for and reducing the risk of and treating bone fracture and osteoporosis comprises *Semen Lactucae sativae, Lignum Aquilariae resinatum, Fructus Oryzae, Resina Boswelliae carterii, Rhizoma atractylodis macrocephalae* and *Semen cuscutae* at the ratio of 0.1-1:2-20:1-5:0.1-1:0.1-1:0.1-1.

2. The pharmaceutical composition of claim 1 wherein said ratio is preferably of 0.5:5:2:0.5:0.25:0.5.

3. The pharmaceutical composition of claim 1 wherein *Lignum Aquilariae resinatum* comprises resin containing *Lignum Aquilariae resinatum*.

4. The pharmaceutical composition of claim 1 wherein *Resina Boswelliae carterii* comprises resin containing *Resina Boswelliae carterii*.

5. The pharmaceutical composition of claim 1 formulated with pharmaceutically acceptable excipients, carriers or diluents to various dosage forms.

6. The pharmaceutical composition of claim 1 formulated with pharmaceutically acceptable excipients, carriers or diluents into lozenge, tablet, film coated tablets, capsule, soft capsule, granule, powder, pill, solution, emulsion, injection solution, injection, ointment, cream, spray or inhalant.

* * * * *